US00PP28582P2

(12) United States Plant Patent
Sato

(10) Patent No.: US PP28,582 P2
(45) Date of Patent: Oct. 31, 2017

(54) ***PODOCARPUS* PLANT NAMED 'MIU'**

(50) Latin Name: *Podocarpus macrophyllus*
Varietal Denomination: Miu

(71) Applicant: Yoshio Sato, Sosa (JP)

(72) Inventor: Yoshio Sato, Sosa (JP)

( * ) Notice: Subject to any disclaimer, the term of this patent is extended or adjusted under 35 U.S.C. 154(b) by 42 days.

(21) Appl. No.: 14/757,375

(22) Filed: Dec. 22, 2015

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

Kawashigeen, Inc. 12th International Flower Expo Tokyo 2015 retrieved on Mar. 30, 2017, retrieved from the Internet at <https://exhibitor.reedexpo.co.jp/IFEX/2015/search/en/detail.phtml?uid=160&eid=4> 1 page.*

Landscape Gardening in Japan, 1912 Chapter 11 Garden Vegetation *Thuya* and *Podocarpus* species retrieved on Mar. 30, 2017, retrieved from the Internet at <http://www.gardenvisit.com/book/landscape_gardening_in_japan_1912/chapter_11_garden_vegetation/thuya_and_podocarpus_species> one page.*

Makuhari Messe 12th International Flower Expo 2015 retrieved on Mar. 30, 2017, retrieved from the Internet at <https://www.m-messe.co.jp/en/event/detail/3677> 2 pp.*

Upov Pluto Plant Variety Database 20170328 retrieved on Mar. 29, 2017, retrieved from the Internet at <www3.wipo.int/pluto/user/en/index.jsp> one page.*

* cited by examiner

*Primary Examiner* — June Hwu
(74) *Attorney, Agent, or Firm* — Penny J. Aguirre

(57) ABSTRACT

A new cultivar of *Podocarpus macrophyllus*, 'Miu', that is characterized by its growth tips and leaves that are yellow-white in color, its variegated foliage that is mottled with yellow and green throughout the leaves, its straight trunk with medium tapering, and its limited branching without pruning.

2 Drawing Sheets

Botanical classification: *Podocarpus macrophyllus.*
Variety denomination: 'Miu'.

CROSS REFERENCE TO A RELATED APPLICATION

This application is related to a plant breeders' rights application filed in Japan on Oct. 27, 2010, application No. 225299. There have been no offers for sale anywhere in the world prior to the filing of this Application and no accessibility to one of ordinary skill in the art could have been derived from printed plant breeder's rights documents.

BACKGROUND OF THE INVENTION

The present invention relates to a new and distinct cultivar of *Podocarpus macrophyllus* and will be referred to hereafter by its cultivar name, 'Miu'. 'Miu' is a new cultivar of evergreen shrub grown for use as a landscape shrub.

The new cultivar arose from an ongoing breeding program commenced by the Inventor in 1975 in Sosa-shi, Chiba, Japan. The new cultivar was discovered as a seedling in 2003 from seed collected from an unnamed and unpatented plant of *Podocarpus macrophyllus* from the Inventor's breeding program. The male parent is unknown.

Asexual propagation of the new cultivar was first accomplished by the Inventor using softwood stem cuttings in Sosa-shi, Chiba, Japan in May of 2003. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Miu' as a unique cultivar of *Podocarpus.*

1. 'Miu' exhibits new growth tips and leaves that are yellow-white in color.
2. 'Miu' exhibits variegated foliage that is mottled with yellow and green throughout the leaves.
3. 'Miu' exhibits a straight trunk with medium tapering.
4. 'Miu' exhibits limited branching without pruning.

The female parent of 'Miu' differs from 'Miu' in having non-variegated solid green foliage. 'Miu' can be compared to the *Podocarpus macrophyllus* cultivars 'Ogon-nagi' (not patented) and 'Aureus' (not patented). Both differ from 'Miu' in having non-variegated foliage. 'Ogon-nagi' differs from 'Miu' in having green foliage. 'Aureus' differs from 'Miu' in having foliage that is yellow-green when grown in full sun.

BRIEF DESCRIPTION OF THE DRAWINGS

The accompanying colored photographs illustrate the overall appearance and distinct characteristics of 4 year-old plants as grown outdoors in a 15-cm containers in Sosa-shi, Chiba, Japan.

The photograph in FIG. 1 provides a view of the overall plant habit and foliage of 'Miu'.

Figure 1:
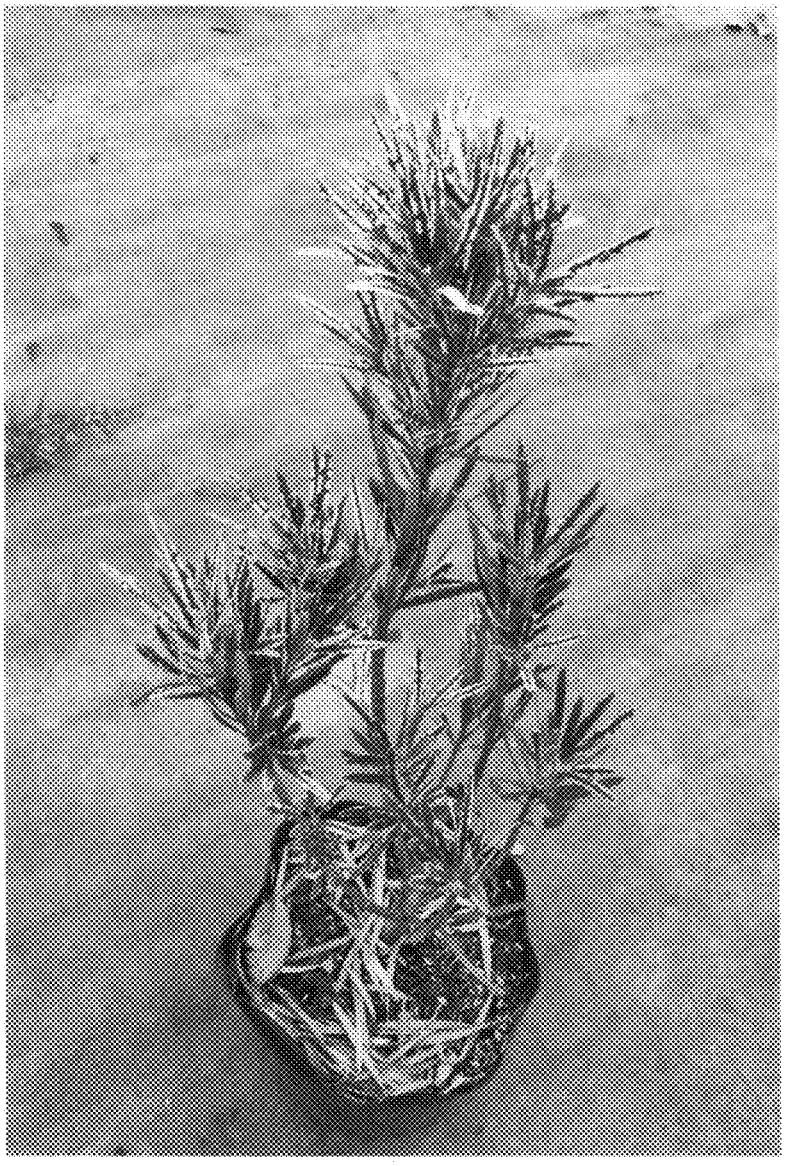
Figure 2:
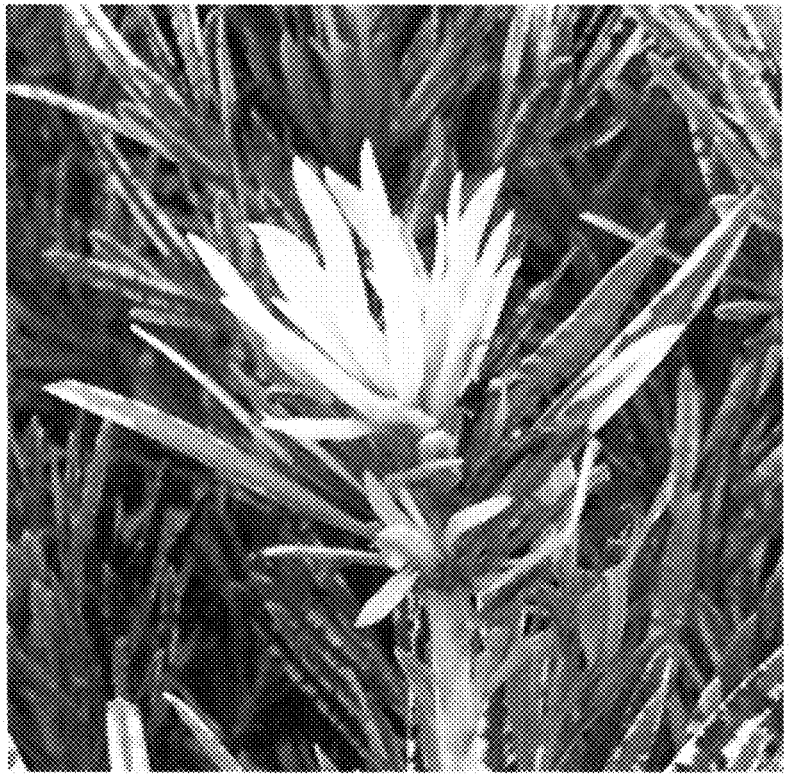

The photograph in FIG. 2 provides a view of the new growing tips of 'Miu'.

The colors in the photographs may differ slightly from the color values cited in the detailed botanical description, which accurately describe the colors of the new *Podocarpus*.

DETAILED BOTANICAL DESCRIPTION

The following is a detailed description of 1 year-old plants of the new cultivar as grown outdoors in three-gallon containers in Luxley, Ala. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Evergreen shrub.

*Plant habit*.—Upright with medium tapering.

*Height and spread*.—Reaches about 34 cm in height and 23 cm in width in a 3-gallon container, mature height in the landscape is 15 to 20 m in height and 5 to 10 m in spread.

*Cold hardiness*.—At least to U.S.D.A. Zones 8b to 11.

*Diseases resistance*.—No susceptibility or resistance has been observed, generally *Podocarpus macrophyllus* is disease free.

*Root description*.—Fibrous.

*Root development*.—Fully root as a young plant in about 6 months.

*Propagation*.—Softwood stem cuttings.

*Growth rate*.—Slow.

Stem description:

*Shape*.—Round to slightly quadrangular.

*Stem color*.—New growth, a color between 150D and 145D with fine ridges of 144C and becoming marked with blotches of 145A; mature bark; 199C and 182C with some areas of 144A showing through bark cracks (as observed on trees six years in age).

*Stem size*.—Main stems; average of 29 cm in length and 6 mm in width (mid stem), lateral branches; average of 11 cm in length and an average of 3 mm in diameter.

*Stem surface*.—New growth; smooth and glabrous with a few fine ridges, mature growth; patches of smooth bark with very fine ridges.

*Branching*.—An average of 3 main stems in a 3-gallon container and an average of 8 lateral branches per main stem.

*Branch internode length*.—Lateral branches in whorls of 3 to 5 branches an average of 7 cm apart.

Foliage description:

*Leaf shape*.—Linear.

*Leaf division*.—Simple.

*Leaf base*.—Attenuate.

*Leaf apex*.—Narrowly acute.

*Leaf fragrance*.—None, but pine scented if crushed.

*Leaf venation*.—Parallel, only midribs of new growth is conspicuous, midrib is slightly raised on upper surface, color on new leaves upper and lower surface; 145A then turning to 137B, color on mature leaves upper and lower surface; 144A.

*Leaf margins*.—Entire.

*Leaf arrangement*.—Whorled.

*Leaf attachment*.—Sessile.

*Leaf internode length*.—Average of 7 mm in length.

*Leaf surface*.—Glabrous and slightly satiny on upper and lower surface.

*Leaf substance*.—Thick and coriaceous.

*Leaf size*.—An average of 5.5 cm in length and 5 mm in width.

*Leaf quantity*.—Average of 50 on a lateral branch 12 cm in length.

*Leaf color*.—Growth tips and new leaves; 11C, newly expanded leaves; upper surface and lower surface 4D with midrib 145A, maturing leaves upper and lower surface; 4D with midrib and mottling of 137B, mature lower leaves; upper surface 137B with faint spots of 137A and NN137A, lower surface 144A with faint spots of 137B.

Inflorescence description: Flowers and fruit have not been observed on any plants currently grown.

It is claimed:

1. A new and distinct cultivar of *Podocarpus* plant named 'Miu' as herein illustrated and described.

* * * * *